United States Patent [19]

Hopp et al.

[11] Patent Number: 4,562,067
[45] Date of Patent: Dec. 31, 1985

[54] PREPARATION OF NOVEL DIBENZOYLMETHANE DERIVATIVE SUNSCREEN AGENTS

[75] Inventors: Rudolf Hopp; Horst Finkelmeier, both of Holzminden; Roland Langner, Bevern, all of Fed. Rep. of Germany

[73] Assignee: Haarmann & Reimer GmbH, Holzminden, Fed. Rep. of Germany

[21] Appl. No.: 570,138

[22] Filed: Jan. 12, 1984

[30] Foreign Application Priority Data

Jan. 22, 1983 [DE] Fed. Rep. of Germany ....... 3302123

[51] Int. Cl.[4] .......................... A61K 7/42; C07C 49/84
[52] U.S. Cl. ...................................... 424/59; 568/331; 568/314
[58] Field of Search ........................... 568/331; 424/59

[56] References Cited

U.S. PATENT DOCUMENTS 3,882,142  5/1975  Walworth et al. ................. 568/331
4,387,089  6/1983  De Polo .

FOREIGN PATENT DOCUMENTS 1959398  6/1970  Fed. Rep. of Germany ........ 424/59
2544180  4/1977  Fed. Rep. of Germany ........ 424/59
2945125  5/1980  Fed. Rep. of Germany ........ 424/59
544052  12/1973  Switzerland ......................... 424/59
1553094  9/1979  United Kingdom .

*Primary Examiner*—James H. Reamer
*Attorney, Agent, or Firm*—Sprung Horn Kramer & Woods

[57] ABSTRACT

The new dibenzoylmethane derivatives of the formula

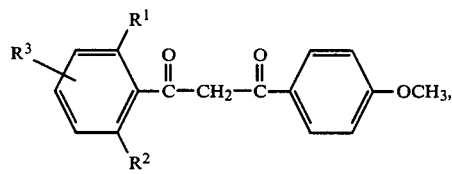

in which
 $R^1$ denotes hydrogen, methyl or ethyl and
 $R^2$ denotes methyl or ethyl and
 $R^3$ represents a straight-chain or branched lower alkyl radical, can be prepared by reacting acetophenone derivatives with an anisic ester or by reacting a substituted benzoic ester with p-methoxyacetophenone. The compounds can be used in sunscreen agents.

6 Claims, No Drawings

PREPARATION OF NOVEL DIBENZOYLMETHANE DERIVATIVE SUNSCREEN AGENTS

The invention relates to new dibenzoylmethane derivatives, processes for their preparation and their use in sunscreen agents.

New dibenzoylmethane derivatives of the formula

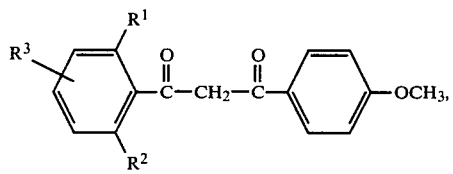

in which
$R^1$ denotes hydrogen, methyl or ethyl and
$R^2$ denotes methyl or ethyl and
$R^3$ represents a straight-chain or branched lower alkyl radical,
have been found.

The straight-chain or branched lower alkyl radical generally contains 1 to, say, 6 carbon atoms. The following lower alkyl radicals may be mentioned as examples: methyl, ethyl, propyl, isopropyl, butyl, isobutyl, tert.-butyl, pentyl, isopentyl, hexyl and isohexyl.

The preferred new dibenzoylmethane derivatives are compounds of the formula

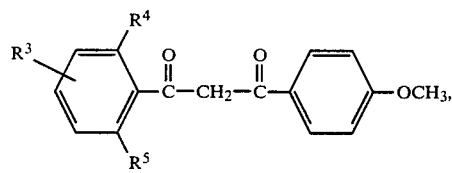

in which
$R^3$ has the abovementioned meaning,
$R^4$ denotes hydrogen or methyl and
$R^5$ denotes methyl.

The following new dibenzoylmethane derivatives may be specifically mentioned: 2-methyl-5-isopropyl-4′-methoxydibenzoylmethane, 2-methyl-5-tert.-butyl-4′-methoxydibenzoylmethane, 2,6-dimethyl-4-tert.-butyl-4′-methoxydibenzoylmethane and 2,4-dimethyl-4′-methoxydibenzoylmethane.

2,4-Dimethyl-4′-methoxydibenzoylmethane is particularly preferred.

The new dibenzoylmethane derivatives can be prepared by reacting, in the presence of a base, alkyl-substituted acetophenone derivatives of the formula

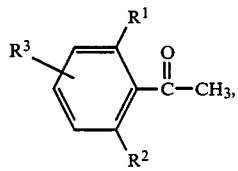

in which
$R^1$, $R^2$ and $R^3$ have the abovementioned meaning, with an anisic ester of the formula

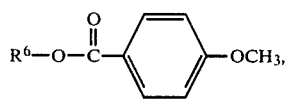

in which
$R^6$ represents a straight-chain or branched lower alkyl radical.

It is also possible to prepare the new dibenzoylmethane derivatives by reacting, in the presence of a base, alkyl-substituted benzoic esters of the formula

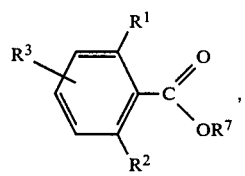

in which
$R^1$, $R^2$ and $R^3$ have the abovementioned meaning, and
$R^7$ represents a straight-chain or branched lower alkyl radical,
with p-methoxyacetophenone.

The bases for the two preparation processes according to the invention are essentially strong bases, such as alkali metal alcoholates, such as sodium or potassium methylate or ethylate, alkali metal hydrides, such as sodium or potassium hydride, or alkali metal amides, such as sodium or potassium amide.

In general, the reactions are carried out in an aprotic solvent which is not changed under the reaction conditions. Examples of solvents which may be mentioned are: toluene, benzene, xylene and diisopropyl ether.

In general, the two preparation processes according to the invention are carried out in the temperature range from 60° to 140° C., preferably from 80° to 120° C., and under normal pressure.

The new dibenzoylmethane derivatives are generally prepared by heating the base in a part of the solvent to the reaction temperature and adding the solution of the two reactants in the major part of the solvent dropwise over a lengthy period.

The dibenzoylmethane derivatives according to the invention exist predominantly in the enol form. The dibenzoylmethane derivatives according to the invention can be advantageously used as the active compound in sunscreen agents. They absorb the ultraviolet radiation of the sun in the so-called UV-A range (320 to 400 nm). UV-A radiation has a deleterious effect on human skin since it can induce pathological changes in the skin, such as, for example, photodermatoses, and it accelerates the ageing of the skin.

Thus the invention also relates to the use of the dibenzoylmethanes according to the invention in sunscreen agents.

The use of certain dibenzoylmethane derivatives for protecting the skin against UV-A radiation has been disclosed. Thus, German Offenlegungsschrift No. 2,544,180 describes alkyldibenzoylmethanes of the formula

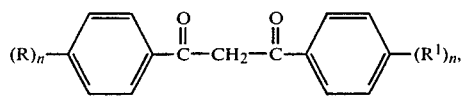 (VI)

in which

R and R[1] represents alkyl groups and n represents 0 to 3 and n' represents 1 to 3.

The absorption maxima of these filter substances are between 330 and 350 nm depending on the type of substitution.

4-tert.-Butyl-4'-methoxydibenzoylmethane, the absorption maximum of which is at 355 nm, is described in German Offenlegungsschrift No. 2,945,125.

In contrast to the dibenzoylmethanes described in German Offenlegungsschrift 2,544,180, the new dibenzoylmethane derivatives according to the invention have the surprising advantage of a markedly higher molar extinction coefficient. Thus, for example, 2,4-dimethyl-4'-methoxydibenzoylmethane according to the invention has a molar extinction coefficient of 30,800, while the compound of most similar structure in German Offenlegungsschrift No. 2,544,180, 2,4-dimethyldibenzoylmethane, has a molar extinction coefficient of only 24,200.

In contrast to the 4-tert.-butyl-4'-methoxydibenzoylmethane in German Offenlegungsschrift No. 2,945,125, the dibenzoylmethanes according to the invention have the advantage that their absorption maxima are in a shorter wavelength range (between 330 and 345 nm) so that, in particular, the more dangerous and higher energy short wavelength UV-A radiation is absorbed. Moreover, the dibenzoylmethane derivatives according to the invention are, surprisingly, more soluble in oil than is 4-tert.-butyl-4-methoxydibenzoylmethane and can more readily be incorporated into the cosmetic bases customarily used for sunscreen agents. The stability to light and heat and the tolerance by the skin of the dibenzoylmethane derivatives according to the invention are well-nigh outstanding. The dibenzoylmethane derivatives according to the invention are colorless and odorless.

Thus, the invention also relates to sunscreen agents which are characterized in that they contain the dibenzoylmethane derivatives according to the invention.

The production of the sunscreen agents according to the invention can be carried out, for example, by incorporating the dibenzoylmethane derivatives according to the invention into a cosmetic base customarily used for sunscreen agents. The incorporation is carried out by distribution methods customarily used, such as, for example, stirring or homogenizing. Examples of customarily used cosmetic bases are creams, lotions, ointments, solutions, sprays and milks (G. H. Nowak, "Die kosmetischen Präparate" (Cosmetic Products), 2nd edition, 1975).

Examples of creams for the sunscreen agents according to the invention are emulsions of the water-in-oil and oil-in-water types.

Examples of lotions for the sunscreen agents according to the invention are alcoholic-aqueous oil and alcohol mixtures.

Examples of ointments for the sunscreen agents according to the invention are pharmaceutical creams.

Examples of solutions for the sunscreen agents according to the invention are solutions of the filter in cosmetic solvents, such as oils and alcohols.

Examples of sprays for the sunscreen agents according to the invention are solutions, combined with a propellent gas.

Milks for the sunscreen agents according to the invention are stable liquid emulsions of the water-in-oil and oil-in-water types.

Depending on the cosmetic base, the content of the dibenzoylmethane derivatives according to the invention in the sunscreen agents is 1 to 6% by weight, preferably 2 to 5% by weight, relative to the cosmetic base.

Obviously, for specific uses, for example medical products, higher doses are also possible.

In general, it is advantageous, in a sunscreen agent which contains UV-A filter, additionally to use a filter substance for the UV-B range (290 to 320 nm). Examples of customarily used UV-B filters which may be mentioned are the compounds listed in German Offenlegungsschrift No. 2,945,125 (foot of page 4 to foot of page 5). The new dibenzoylmethane derivatives are particularly preferably combined with UV-B filter substances, such as 2-ethylhexyl p-methoxycinnamate or isoamyl p-methoxycinnamate.

The ratio of dibenzoylmethane derivatives according to the invention of UV-B filters in the sunscreen agents according to the invention is generally 1:3 to 2:1.

EXAMPLE 1

A solution of 148 g of 2,4-dimethylacetophenone (1.0 mol) and 332 g of methyl anisate (2.0 mol) in 180 g of toluene is added dropwise within 3 hours to a stirred suspension of 36 g (1.5 mols) of sodium hydride in 180 g of dry toluene at 100° C. under nitrogen. Hydrogen is liberated during the introduction, and the reaction mixture becomes highly viscous. After the addition is complete, the mixture is stirred at 100° C. for a further 3 hours, then cooled down to room temperature and 400 ml of water, 170 g of concentrated hydrochloric acid and 800 ml of ethyl acetate are added. The insoluble constituents are filtered off and the aqueous phase is separated from the filtrate. The organic phase is washed with water, the ethyl acetate is removed and the residue is distilled in vacuo to recover the excess methyl anisate. 138 g of unreacted methyl anisate are obtained. The residue is recrystallized from a mixture of isopropanol and toluene. 198 g (70.2% of theory) of 2,4-dimethyl-4'-methoxydibenzoylmethane are obtained.

Melting point=48° C., UV spectrum: max=345 nm, E (1%, 1 cm)=1090.

EXAMPLE 2

2,4-Diethyl-4'-methoxydibenzoylmethane is obtained in analogy to Example 1 from 2,4-diethylacetophenone and methyl anisate in the presence of sodium hydride.

Melting point=38° C., UV spectrum: max=344 nm, E (1%, 1 cm)=1020.

EXAMPLE 3

2,6-Dimethyl-4-tert.-butyl-4'-methoxydibenzoylmethane is obtained in analogy to Example 1 from 2,6-dimethyl-4-tert.-butylacetophenone and methyl anisate.

Melting point=108° C., UV spectrum: max=333 nm, E (1%, 1 cm)=850.

EXAMPLE 4

2-Methyl-5-isopropyl-4'-methoxydibenzoylmethane is obtained in analogy to Example 1 from 2-methyl-5-isopropylacetophenone and methyl anisate in the presence of sodium hydride.

Melting point=74° C., UV spectrum: max=343 nm, E (1%, 1 cm)=980.

EXAMPLE 5

2-Methyl-5-tert.-butyl-4'-methoxydibenzoylmethane is obtained in analogy to Example 1 as a viscous oil, which is purified by column chromatography on silica gel, from 2-methyl-5-tert.-butylacetophenone and methyl anisate in the presence of sodium hydride.

UV spectrum: max=345 nm, E (1%, 1 cm)=760.

EXAMPLE 6

2,5-Dimethyl-4'-methoxydibenzoylmethane is obtained in analogy to Example 1 from 2,5-dimethylacetophenone and methyl anisate in the presence of sodium hydride.

Melting point=87° C., UV spectrum: max 342 nm, E (1%, 1 cm)=1010.

SUNSCREEN MILK (O/W EMULSION TYPE)

(A)

3.50% of mono, di and tri(alkyl tetraglycol ether) o-phosphate emulsifier
1.50% of oxethylated polyglycerol stearate emulsifier
0.80% of cetyl alcohol
3.00% of light liquid paraffin
5.00% of isopropyl myristate
4.50% of 2-ethylhexyl p-methoxycinnamate
2.50% of 2-methyl-5-tert.-butyl-4'-methoxydibenzoylmethane
0.05% of propyl p-hydroxybenzoate (B)

73.80% of distilled water
0.15% of methyl p-hydroxybenzoate
3.00% of a 70% strength aqueous solution of sorbitol
0.20% of imidazolidinylurea derivative
0.30% of carboxyvinyl polymer
1.20% of a 10% strength solution of sodium hydroxide
0.50% of perfume oil

PRODUCTION PROCEDURE

Part A: The components are mixed and heated at 80°-85° C. until a clear melt is formed.
Part B: The carboxyvinyl polymer is dispersed in water until there are no lumps. Then the sorbitol, methyl p-hydroxybenzoate and imidazolidinylurea derivative are added and the mixture is heated to 90° C. It is then neutralized with sodium hydroxide, and Part B is stirred into Part A. The emulsion is then cooled to 40° C. with stirring, and the perfume oil is added and the mixture is further cooled to room temperature with stirring.

SUNSCREEN OIL LOTION 43.50% of polyoxypropylene(15) stearyl ether
11.00% of isopropyl myristate
6.00% of 2-ethylhexyl p-methoxycinnamate
3.00% of 2-methyl-5-isopropyl-4'-methoxydibenzoylmethane
35.00% of 96% by volume denatured ethyl alcohol
1.00% of liquid lanolin
0.50% of perfume oil

PRODUCTION PROCEDURE

The 2-methyl-5-isopropyl-4'-methoxydibenzoylmethane is dissolved, warming slightly (40°-50° C.), in the mixture of polyoxypropylene(15) stearyl ether, isopropyl myristate and 2-ethylhexyl-p-methoxycinnamate. Then the remaining constituents are incorporated by stirring in sequence.

SUNSCREEN OIL 15.00% of isopropyl myristate
20.00% of refined coconut oil
6.00% of isoamyl p-methoxycinnamate
4.00% of 2,4-dimethyl-4'-methoxydibenzoylmethane
53.50% of light liquid paraffin
1.00% of liquid lanolin
0.50% of perfume oil

PRODUCTION PROCEDURE 2,4-Dimethyl-4'-methoxydibenzoylmethane is dissolved, warming slightly (40°-50° C.), in the mixture of isopropyl myristate, coconut oil and isoamyl-p-methoxycinnamate. Then the remaining constituents are incorporated by stirring in sequence.

SUNSCREEN CREAM (W/O EMULSION TYPE)

(A)

20.00% of a combination of nonionic fatty acid esters of polyhydric alcohols with waxes and purified saturated hydrocarbons
4.00% of isoamyl p-methoxycinnamate
4.00% of light liquid paraffin
3.00% of decyl oleate
4.00% of 2,4-diethyl-4'-methoxydibenzoylmethane
0.15% of propyl p-hydroxybenzoate (B)

58.30% of distilled water
0.15% of methyl n-hydroxybenzoate
0.20% of imidazolidinylurea derivative
0.50% of magnesium sulphate.7H$_2$O
5.00% of a 70% strength aqueous solution of sorbitol
0.70% of perfume oil

PRODUCTION PROCEDURE

Part A: The constituents are mixed and heated to 85° C.
Part B: The aqueous phase is heated to 90° C. and then incorporated into Part A with stirring. The perfume oil is added to the emulsion at a temperature of the emulsion of 40° C.

The mixture is then homogenised using a colloid mill or roller mill.

It will be appreciated that the instant specification and examples are set forth by way of illustration and not limitation, and that various modifications and changes may be made without departing from the spirit and scope of the present invention.

What is claimed is:

1. 2,4-Dimethyl-4'-methoxydibenzoylmethane of the formula

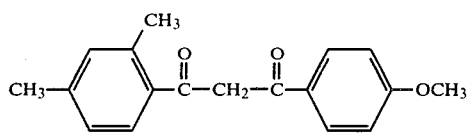

2. A sunscreen composition comprising a sunscreen base and a sun-screening effective amount of a dibenzoylmethane derivative according to claim 1.

3. A sunscreen composition according to claim 2, wherein the dibenzoylmethane derivative is present in about 1 to 6% by weight.

4. A composition according to claim 2, further containing a sun-screening effective amount of a compound which absorbs UV radiation of 290 to 320 nm.

5. A process for protecting the skin from UV radiation which comprises applying to the skin a sun-screening effective amount of a compound according to claim 1.

6. The method according to claim 4, wherein there is also applied to the skin a sun-screening effective amount of a compound which absorbs UV radiation of 290 to 320 nm.

* * * * *